United States Patent [19]

Huc et al.

[11] Patent Number: 4,814,120
[45] Date of Patent: Mar. 21, 1989

[54] PROCESS FOR THE PREPARATION OF COLLAGEN TUBES

[75] Inventors: Alain Huc, Sainte-Foy-Les-Lyon; René Gimeno, Pelussin, both of France

[73] Assignee: Bioetica S.A., Lyons, France

[21] Appl. No.: 41,652

[22] Filed: Apr. 21, 1987

Related U.S. Application Data

[63] Continuation of Ser. No. 703,890, Feb. 21, 1985, abandoned.

[30] Foreign Application Priority Data

Feb. 21, 1984 [FR] France ............... 8403181

[51] Int. Cl.$^4$ .................... D01F 4/00; D01D 5/06
[52] U.S. Cl. ............................ 264/28; 264/101; 264/558; 264/561; 264/562; 264/202; 264/209.1; 264/234; 264/236; 264/232; 264/340; 264/345; 264/347; 128/DIG. 8; 623/1; 623/12
[58] Field of Search ............ 264/183, 202, 209.1, 264/209.5, 558, 561, 562, 177.14, 28, 101, 234, 236, 232, 340, 345, 347; 128/334 R, DIG. 8; 623/1, 12; 210/500.23, 500.27

[56] References Cited

U.S. PATENT DOCUMENTS

| | | | |
|---|---|---|---|
| 2,161,908 | 6/1939 | Becker | 425/380 X |
| 2,345,086 | 3/1944 | Becker et al. | 425/380 |
| 2,847,713 | 8/1958 | Weingand | 264/209.1 X |
| 3,122,788 | 3/1964 | Lieberman | 264/108 |
| 3,194,865 | 7/1965 | Fagan et al. | 264/209.1 |
| 3,483,286 | 12/1969 | Duffy et al. | 264/202 |
| 3,551,560 | 12/1970 | Thiele | 623/1 |
| 3,630,760 | 12/1971 | Taylor | 425/70 X |
| 3,688,317 | 9/1972 | Kurtz | 128/334 R X |
| 3,927,422 | 12/1975 | Sawyer | 128/334 |
| 4,082,507 | 4/1978 | Sawyer | 128/1 R |
| 4,156,067 | 5/1979 | Gould | 128/334 |
| 4,319,363 | 3/1982 | Ketharanathan | 623/1 |
| 4,466,139 | 8/1984 | Ketharanathan | 623/1 |
| 4,476,072 | 10/1984 | Ariëns | 264/202 X |

FOREIGN PATENT DOCUMENTS

| | | |
|---|---|---|
| 2235133 | 6/1973 | France. |
| 76922 | 2/1979 | Romania. |

OTHER PUBLICATIONS

The Journal of Toxicological Sciences, vol. 7, Supplement II, pp. 63–91, 1982.
"Le Collagene: Proprietes Mecaniques des Films et Thermostabilite de la Molecule"–A. Huc–pp. 307–310.
"Long Term Behavior of Bovine Collagen Membrane used as Vascular Substitute", Elza Chignier et al.
"Revue de L'Institut Pasteur de Lyon", 1978, No. 2, pp. 179–190.

Primary Examiner—Jan H. Silbaugh
Assistant Examiner—Hubert C. Lorin
Attorney, Agent, or Firm—Herbert Dubno; Jonathan Myers

[57] ABSTRACT

A process for preparing collagen tubes includes extruding an aqueous gel containing about 1.5% native collagen through a cylindrical spinneret equipped with a central concentric tube designed to receive a part of a coagulation bath, followed by coagulation of the internal and external walls of the tube, leaving the spinneret in a coagulation bath constituted by about 70% acetone and 30% ammonia, followed by drying. Following drying, the collagen tube may be subjected to reticulation by dehydration carried out at about 80° C. under a pressure of about 0.1 mm of Hg (vacuum) for about 24 hours. The reticulated collagen tube may eventually be subjected to a treatment which permits the introduction of azide groups onto the molecule without requiring that the collagen be coupled to any external molecule.

10 Claims, 1 Drawing Sheet

U.S. Patent    Mar. 21, 1989    4,814,120
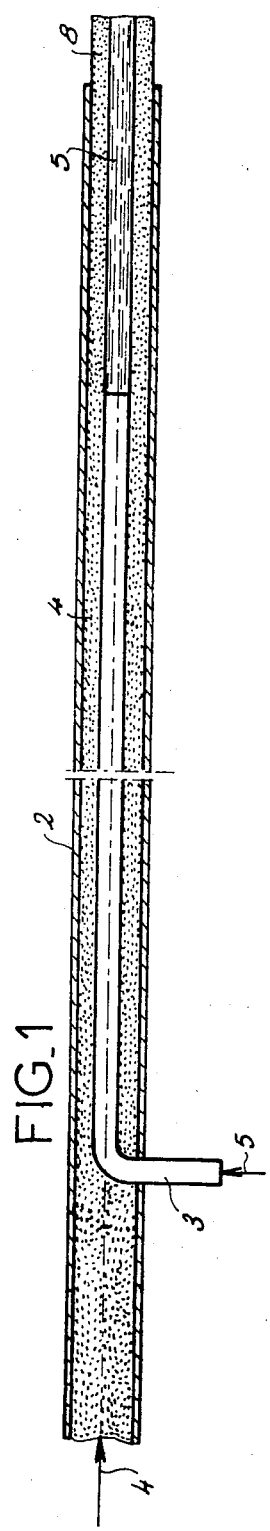
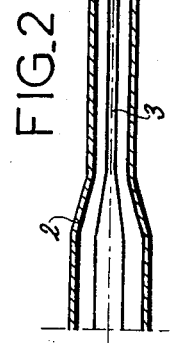
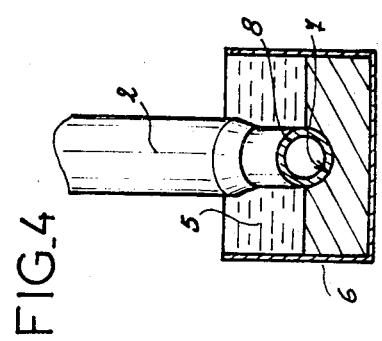
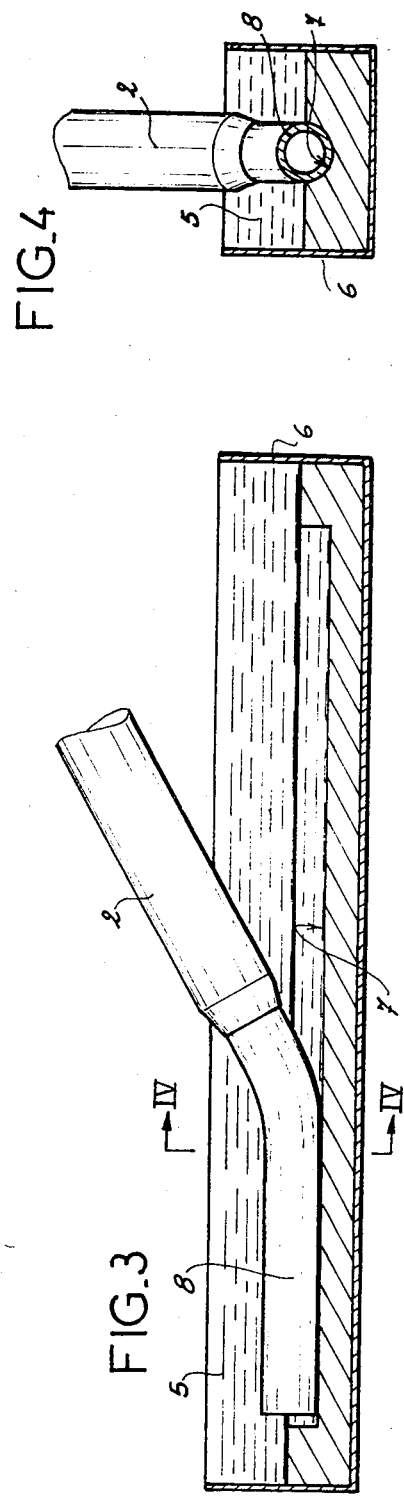

PROCESS FOR THE PREPARATION OF COLLAGEN TUBES

This is a continuation of co-pending application Ser. No. 703,890, filed on Feb. 21, 1985, now abandoned.

FIELD OF THE INVENTION

Our present invention relates to a process for the preparation of collagen tubes, especially tubes of a small diameter and the use of the collagen tubes thus obtained for vascular prosthetic and nerve-suture applications.

BACKGROUND OF THE INVENTION

Collagen, which constitutes about 40% of the protein in a living being, is the support substance for conjunctive tissue, and is necessary for the tissue to function.

Collagen possesses remarkable mechanical properties, has good hemostatic properties, and exerts an influence on cellular growth.

In addition to these properties, there are two other interesting collagen characteristics: its biocompatibility and its biodegradability.

The collagen macromolecule having a length of about 3000 Å and a width of about 15 Å is constituted by three peptide chains. Each chain has a mass of 100,000 daltons, and is in helicoidal form. The axes of the helices extend helically around a common axis through the interior of the macromolecule. Between certain peptide chains, there exist reticulated or cross-link bonds. The ordered arrangement of the macromolecules between these peptide chains leads to formation of fibers.

The excellent mechanical properties of collagen are provided in large part, by the helicoidal structure and the reticulated bonds.

The antigenic character of collagen is also very low. Consequently collagen originally from an animal does not provoke an action of rejection when applied in vivo to a human being, according to a study conducted by Takeda, U. et al and appearing in the *Journal of Toxicology Sciences*, Vol. 7, Suppl. II, pp 63-91 (1982).

There are two important advantages to collagen which make it readily adaptable to be used in vascular prostheses: on the one hand its biocompatibilitiy and on the other hand its ability to exert an action in cellular growth. Conversely, in these applications, there are two drawbacks: its biodegradability and its hemostatic ability. This latter property is especially troublesome because of the risk of provoking thromboses and there is also the problem of the disappearance of the prosthesis by destruction of the helicoidal structure of the protein which results in poor mechanical properties. Finally the biodegradability of the collagen must be sufficiently low so that it can be reestablished by the cells before it is digested by the enzymes.

It is known that synthetic vascular prostheses are not really satisfactory if their diameters are greater than 4 mm. Above this dimension, the replacement vessels possess a serious inconvenience, in particular their level of effectiveness is low. That is why it is obviously important to find a way to fill this need wtih the aid of a collagen-based biomaterial which will be of some help in the field of vascular prostheses.

Previously the use of resinous heterografts has been revealed to be an asset and has brought about some interesting results.

Unfortunately, this technique is very costly and the number of applications to the veins is very limited. That is why it is necessary to be able to prepare tubes of a small diameter based on collagen.

Roumanian Pat. No. 76 922 describes a process and an apparatus to obtain tubular elements starting from collagen gel; in this process the collagen is put into solution and subjected to dialysis using distilled water to which is added EDTA and a tubular element containing collagen is thus formed by an electrodeposition technique. Besides the fact that such a technique is difficult to put into practice, it may be noted that the Roumanian inventors do not give any indication of what is the minimum diameter of the tubes which are obtained by such a process.

In a lecture presented by Chigner, E., Huc, A. and Eloy, R. at the Eighteenth Congress of the European Society of Surgical and Stress Research in May 1982, the biocompatibility of collagen was emphasized and the ability of this material to function in making vascular prostheses was determined according to the following tests:

A sample constituted by a collagen very close to that of the collagen in the tubes described hereinafter was sutured onto the aorta of a rat, the aorta having previously been perforated. The results obtained indicated a good biocompatibility of the material, the absence of blood coagulation upon contact with the collagen, and finally a mechanical resistance sufficient to withstand blood pressure.

OBJECT OF THE INVENTION

It is the object of the invention to provide a process for obtaining collagen tubes starting from collagen and having a diameter less than 4 mm which can be applied in the field of vascular prosthesis and which possess a sufficiently low biodegradability as well as a satisfactory stability.

SUMMARY OF THE INVENTION

The object of the invention is attained by the process according to the invention which includes the following steps: extruding in a cylindrical spinneret equipped with a central concentric tube designed to receive a portion of a coagulation bath, an aqueous acidic gel containing about 1.5% native collagen, followed by coagulating of the internal and external walls of the tube leaving the spinneret in a coagulant bath constituted by about 70% acetone and 30% ammonia; followed by drying, and finally by an eventual reticulation of the collagen tube.

The tube leaving the spinneret is advantageously maintained for about 2 hours in the coagulant bath.

According to one feature of the invention, the drying of the tube is carried out in free air.

According to another method of carrying out the invention, the drying of the tube is carried out by lyophilization.

The reticulation of the collagen is advantageously carried out by dehydration in an oven at about 80° C. under a vacuum (pressure of about 0.1 mm Hg) for a period of about 24 hours.

According to a preferred feature, the collagen tubes, once reticulated, are subjected to a treatment which permits the introduction of azide groups in the molecule, without, however, causing coupling with any molecule external to the collagen.

In effect, it can be said that by programmed differential calorimetry, that the temperature of the start of the denaturation of collagen is of the order of 34° C., which means that denaturation will occur at temperatures lower than that of the organism. Such denaturation contributes to the loss of the implanted material as well as to the loss of some of the mechanical properties. See Huc, *A. Labo Pharm.*, 275, 307–312 (1978).

The abovementioned introduction of the azide groups into the collagen molecule permits increasing the denaturation temperature without bonding external molecules, which often contains biologically harmful materials in general, and which in particular are harmful to cellular development. The process increases by about 10° C., the temperature at which denaturation starts. Such a temperature is certainly much higher than that of the human being which is 37° C.

It must be noted, however, that the stabilization in chemical terms of the protein is not necessary when the tube implanted must be subject to significant mechanical constraints or if a low biodegradability is required of the biomaterial.

Generally, the process to introduce the azide groups in the collagen molecule can be equally applied to heterografts, in which they play the same role as they do in collagen tubes, and which permits avoiding the use of glutaraldehyde, which is often a source of calcification, in particular in the case of cardiac valves.

BRIEF DESCRIPTION OF THE DRAWING

Our present invention is more fully described along with its advantages in the description which follows, reference being made made to the attached schematic drawing in which:

FIG. 1 is a schematic sectional view of a spinneret designed for extrusion according to the invention for preparing collagen tubes having a diameter greater than 2mm.

FIG. 2 is a schematic sectional view of another apparatus for carrying out the invention where the spinneret is specifically adapted for the extrusion of collagen tubes having an internal diameter less than 2 mm;

FIG. 3 is a schematic sectional view of an apparatus which serves the purposes of coagulating the collagen tubes; and FIG. 4 is a section view taken along the line IV—IV in FIG. 3.

SPECIFIC DESCRIPTION AND EXAMPLE

In FIGS. 1–4, element 2 represents the body of a spinneret supplied by an interior concentric conduit 3 with a portion (circulated by a pump) of the coagulation bath, the collagen gel is represented as 4 and the coagulation bath as 5. Element 6 is a tank containing the coagulation bath. Element 7 is a female cylindrical support and element 8 is the tube obtained.

The process for the fabrication of the collagen tubes according to the invention comprises essentially three steps which will now be described in detail:
preparation of the collagen gel;
extrusion and coagulation of the tube; and
treatment of the tube with a view toward improving its behavior in vivo.

Preparation of the Collagen Gel

Hides obtained from freshly slaugthered calves washed with water. The hair and the subcutaneous tissues are mechanically eliminated by the aid of a splitting apparatus and only the skin is saved. The latter is then chopped and ground. The ground product is then washed with a phosphate-containing buffer at a pH of 7.8, then rinsed with deionized water. It is then placed in an acetic acid solution at a pH of 3.5. The dilution must be such that the concentration of collagen must be about 1.5%. The mixture is then homogenized by ultrasonic waves, then degassed by agitation under vacuum.

Formation of Collagen Tubes

The collagen gel 4 obtained by the abovementioned process is extruded in the cylindrical spinneret 2. The originality of this spinneret is that it contains an interior conduit 3 concentric to the conduit where the collagen gel enters. The conduit 3 serves to introduce the liquid coagulant 5 to the interior of the collagen gel and this results in obtaining collagen in the form of a tube having a diameter that will be less than the diameter of the conduit. A screw-feed, endless advancement system permits displacement of the spinneret at a constant rate, and which is adjustable with respect to the coagulant bath mentioned above. The coagulated tube 8 is deposited on a female cylindrical support 7 of the same diameter as the tube placed in the coagulation tank 6. The system prevents crushing of the tube in the coagulant bath.

As can be seen from FIG. 2, the diameter of the head of the spinneret is diminished when it is desired to extrude the tubes at a diameter of 2 mm or even 1 mm.

The tubes thus formed are allowed to remain undisturbed for about 2 hours in the coagulant bath. At the end of this time period, the tubes are again filled with water and are placed on a rod of polytetrafluoroethylene (P.T.F.E.) (rod not represented) of the same diameter and dried in the air. After drying, the tube is able to be easily removed from the support.

The coagulated tube can also be dried by lyophilization. In that case the obtained dry tube has a spongy structure and the walls are much thicker than the walls of a tube obtained by drying in air.

The obtained materials are analyzed in three ways: chemical analysis, molecular mass analysis and structural analysis. The first analysis is done to determine how pure the collagen is. The second analysis is done to determine the strength of the peptide chains and the third analysis is done to make sure that the helicoidal structure of the protein is not destroyed. All of these analyses are necessary in order to make sure that the protein possesses all of the collagen properties (Huc A. and Bartholin F. Review of the Pasteur Institute of Lyon, Vol. 11, No. 2, pp 179–190, 1978).

Treatment of the Tube (a) Reticulation (cross-linking) of Collagen

In order to strengthen the resistance of the protein, the material is dehydrated in a stove at 80° C. under a vacuum (0.1 mm Hg) for 24 hours. Such a treatment creates new reticulated bonds between the peptide chains of the collagen and thereby augments its insolubility and diminishes its biodegradability.

(b) Improvement in the Stability of Collagen by Introduction of Azide in the Molecule We have determined in effect that it is possible to improve the stability of the collagen tubes by subjecting same to a treatment which permits the introduction of azide groups in a molecule without having to couple the collagen molecule to an external substance, such as in the process described and claimed in French Pat. No. 2 235 133.

The material is placed for 8 days in an acidic methanol solution (pure methanol plus 0.3N HCl). As a result the acidic free carboxy groups of the collagen are methylated according to the following reaction:

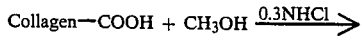

The acid groups are those of aspartic acid or glutamic acid.

The material is next thoroughly washed with water and then placed in 1% aqueous solution of hydrazine. The methyl groups are then transformed into hydrazide groups according to the following reaction:

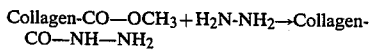

A treatment time of 4 or 5 hours is necessary in order to obtain the maximum number of transformed groups. The material is then thoroughly mixed with water and then subjected to the action of a solution of sodium nitrite in 0.3N HCl. The one obtains the azide-substituted collagens according to the following reaction:

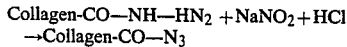

The total duration of this reaction is about 5 minutes. The material is then placed for about 2 hours in a borate buffer at a pH of 9 (boric acid, sodium tetraborate 0.2M) and then thoroughly mixed with water.

All of the process steps are carried out at ambient temperature (20° C.).

The tests carried out on the final material show that it contains no hydrazine, no sodium nitrite, and no other external substance.

Programmed differential calorimetry indicates that the denaturation temperature of collagen is about 10° C. higher for collagen thus treated than it is for untreated collagen than it is for collagen subjected to a simple reticulation process. Active collagen is thus more stable than reconstituted collagen. The denaturation temperature of the collagen thus prepared exceeds 37° C., normal body temperature. Thus the collagen will conserve all of its native structure, which is essential for its properties, especially mechanical properties. Furthermore the collagen treated according to the new invention is better resistant to the attack of proteolytic enzymes.

A film of collagen thus treated has been implanted in a rat, both intraperitoneally and subcutaneously. Its behavior in vivo has been compared to that of a film of raw collagen placed in the same position but not treated according to the present invention.

The results of the examination are as follows:

After 21 days, the raw film has vanished, whereas after 90 days, the active film of the invention is always identifiable.

Mesothelial cells exist on the two implants but their appearance is retarded on the active material and the cells develop there less well.

Finally, a biodegradability which is more or less significant, can be obtained by modifying the contact time of the collagen with the methyl alochol in the first step of the treatment to introduce the azide substituents. A lower contact time results in the diminution of the number of blocked acid groups, and as a result, less protection of the collagen. Thus, in the latter case, the biodegradability of the material will be more important than in the complete azide-forming treatment.

(c) Sterilization

The tube is subjected to a radiation treatment of 2,5 Mrad. Each of the radiation doses eliminates all microorganisms, reticulates the collagen, and diminishes its hemostatic ability.

The process according to the invention thus permits obtaining simple tubes, altogether adapted to forming vascular prostheses, and having an internal diameter of between 1 and 10 mm.

The results of the physical-chemical and mechanical analysis of the tubes thus obtained are as follows:

| Chemical Analysis | |
| --- | --- |
| Dried Residue at 105° C. | 86.3 |
| Mineral Material | 0.61 |
| Acidity (based on acetic acid) | 0.33 |
| Nitrogen | 14.6 |
| Total Protein | 79.7 |
| Hydroxyproline | 9.88 |
| Collagen | 73.7 |

The quantities are given in grams per number of grams of raw product.

| Physical Analysis | |
| --- | --- |
| X-Ray Diffraction | Put into evidence to show the helicoidal structure |
| Programmed Differential Calorimetry | |
| temperature before denaturation | 34.3° C. |
| temperature at the end of denaturation | 49.7° C. |
| $\Delta$ H in joules per mg of collagen where the percentage of helicoidal structure is 87%. | $4.2 \times 10^{-2}$ |

Mechanical Tests

Rupture Strain in $Kgf/cm^2 = 0.608$ (coefficient variation 20%)

Rupture of Elongation in per cent = 13 (coefficient variation 55%)

Modulus of Elasticity in $kgf/cm^2 = 11.422$ (coefficient variation 12%)

The elevated value for the rupture strain expressed in $kgf/cm^2$ is noteworthy.

When the collagen tubes have been treated according to the present invention, that is, the new stabilization process described above, the results of the programmed differential calorimetry are as follows:

| | |
| --- | --- |
| starting temperature of denaturation | 47° C. |
| ending temperature of denaturation | 67° C. |

In respect to a collagen tube not treated according to the invention, there is a temperature of 13° C. in the case of the first figure and 8° C. in the case of the second figure.

There are situations where a simple wall may not be able to provide sufficient mechanical properties when the prostheses are subjected to great mechanical constraints. In that case the collagen prostheses can be constructed either by two concentric collagen tubes, bonded to one another by a biological adhesive of the type Tissucol or by two collagen tubes between which is located a synthetic thread, for example a polyester.

In the following table respective compliance values are given for a human saphenous vein, for a synthetic prosthesis (Gore-Tex), for a collagen tube and for two tubes of collagen strengthened by polyester thread.

The results have been obtained from the Laboratory of Biorheology and Hydrodynamic Physiology at the University of Paris VII (H. Flaud).

| Range of Pressure in mm of Hg | Compliance in mm (mb/m) | |
| --- | --- | --- |
| Prostheses | 50 | 100–200 |
| Human Saphenous Vein | 14.2 | 4.5 |
| Gore-Tex (diameter 4 mm) | 2.7 | 2.7 |
| Collagen (diameter 4 mm) | 21.5 | 11.6 |
| Reinforced Collagen (diameter 4 mm) | 5.6 | 5.6 |

The results show that a simple collagen tube has a compliance higher than that of the saphenous vein and that the compliance of the collagen prostheses reinforced by synthetic thread is more elevated than that of the Gore-Tex prostheses.

The tubes of a small diameter can be partially utilized in forming nerve sutures. The experiments conducted in this field have shown that the biomaterial has permitted the formation of nerve junctions with good results.

We claim:

1. A process for the preparation of a collagen tube having a diameter less than 4mm to be used as vascular prostheses or as nerve sutures which comprises the steps of:
   (a) extruding an aqueous acid gel containing about 1.5% native collagen thereby forming an extruded tube consisting of collagen and having internal and external walls and a diameter less than 4mm;
   (b) coagulating the internal and external walls of the collagen tube formed in step (a) in a coagulation bath constituted by about 70% acetone and 30% ammonia; and
   (c) drying the collagen tube.

2. The process defined in claim 1 wherein the diameter of the collagen tube is less than 2 mm.

3. The process defined in claim 1, wherein in step (a) the extruding is carried out in a cylindrical spinneret equipped with a central concentric conduit designed to receive a portion of the coagulation bath, as defined in step (b).

4. The process defined in claim 3 wherein the collagen tube extruded from the spinneret is deposited on a female cylindrical support of the same diameter as that of the collagen tube and maintained for about 2 hours in the coagulation bath.

5. The process defined in claim 1 wherein in step (c) the drying is carried out in free air.

6. The process defined in claim 1 wherein in step (c) the drying is carried out by lyophilization.

7. The process defined in claim 1 wherein the collagen tube, after drying according to step (c), is subjected to reticulation by dehydration carried out at about 80° C. under a vacuum for about 24 hours.

8. A process for the preparation of a collagen tube having a diameter less than 4 mm to be used as a vascular prosthesis or as a nerve suture, which comprises the steps of:
   (a) extruding an aqueous acid gel containing about 1.5% native collagen thereby forming an extruded tube consisting of collagen and having internal and external walls and a diameter less than 4 mm;
   (b) coagulating the internal and external walls of the collagen tube formed in step (a) in a coagulation bath constituted by about 70% acetone and 30% ammonia;
   (c) drying the collagen tube;
   (d) reticulating the dried collagen tube by dehydration carried out at about 80° C. under a vacuum for about 24 hours; and
   (e) subjecting the reticulated collagen tube to a treatment which permits introduction of azide groups in the collagen without resulting in coupling of the collagen to any external molecule.

9. The process for preparing the collagen tube defined in claim 8 wherein the treatment in step (e) to permit introduction of azide groups in the collagen comprises:
   (i) methylating free acid collagen groups by contact with methyl alcohol to form corresponding methyl ester groups;
   (ii) transforming the methyl ester groups to hydrazide groups by reaction with hydrazine; and
   (iii) converting the hydrazide groups to azide groups by reaction with nitrous acid.

10. The process for preparing the collagen tube defined in claim 9, wherein contact time of the collagen with the methyl alcohol in step (i) is regulated as a function of biodegradability.

* * * * *